（12） United States Patent
McVenes et al.

(10) Patent No.: US 7,313,445 B2
(45) Date of Patent: Dec. 25, 2007

(54) MEDICAL LEAD WITH FLEXIBLE DISTAL GUIDEWIRE EXTENSION

(75) Inventors: Rick D. McVenes, Isanti, MN (US); Kenneth B. Stokes, Anoka, MN (US)

(73) Assignee: Medtronic, Inc., Minneapolis, MN (US)

( * ) Notice: Subject to any disclaimer, the term of this patent is extended or adjusted under 35 U.S.C. 154(b) by 569 days.

(21) Appl. No.: 10/255,261

(22) Filed: Sep. 26, 2002

(65) Prior Publication Data

US 2004/0064172 A1 Apr. 1, 2004

(51) Int. Cl.
*A61N 1/05* (2006.01)
(52) U.S. Cl. ..................................... 607/127
(58) Field of Classification Search ............... 607/115, 607/116, 119, 120, 122, 123, 125–128
See application file for complete search history.

(56) References Cited

U.S. PATENT DOCUMENTS

| | | | |
|---|---|---|---|
| 4,355,646 A | 10/1982 | Kallok | |
| 4,488,561 A * | 12/1984 | Doring | 607/125 |
| 4,506,680 A | 3/1985 | Stokes | |
| 4,932,407 A * | 6/1990 | Williams | 607/5 |
| 4,972,848 A | 11/1990 | Di Domenico | |
| 4,984,581 A | 1/1991 | Stice | |
| 5,067,489 A | 11/1991 | Lind | |
| 5,246,014 A | 9/1993 | Williams | |
| 5,282,414 A | 2/1994 | Chen | |
| 5,342,414 A | 8/1994 | Mehra | |
| 5,509,411 A | 4/1996 | Littmann | |
| 5,531,781 A * | 7/1996 | Alferness et al. | 607/122 |
| 5,545,206 A * | 8/1996 | Carson | 607/126 |
| 5,584,873 A | 12/1996 | Shoberg | |
| 5,935,160 A | 8/1999 | Auricchio | |
| 6,006,122 A * | 12/1999 | Smits | 600/373 |
| 6,192,280 B1 | 2/2001 | Sommer | |
| 6,366,819 B1 | 4/2002 | Stokes | |
| 6,493,591 B1 * | 12/2002 | Stokes | 607/127 |
| 6,714,823 B1 * | 3/2004 | De Lurgio et al. | 607/122 |
| 2003/0220677 A1 * | 11/2003 | Doan et al. | 607/122 |

* cited by examiner

*Primary Examiner*—George R. Evanisko
(74) *Attorney, Agent, or Firm*—Michael C. Soldner; Paul H. McDowall

(57) ABSTRACT

An implantable medical lead is provided with a distal guidewire extension. A flexible distal guidewire extension, which may take the form of a helically wound wire around a tapered core, extends from the distal end of a lead body. The extension may exit a tip electrode, which may be a generally rounded electrode or an active fixation electrode. The distal guidewire extension is preferably insulated, but may be provided with an uninsulated segment for serving as an electrode.

12 Claims, 5 Drawing Sheets

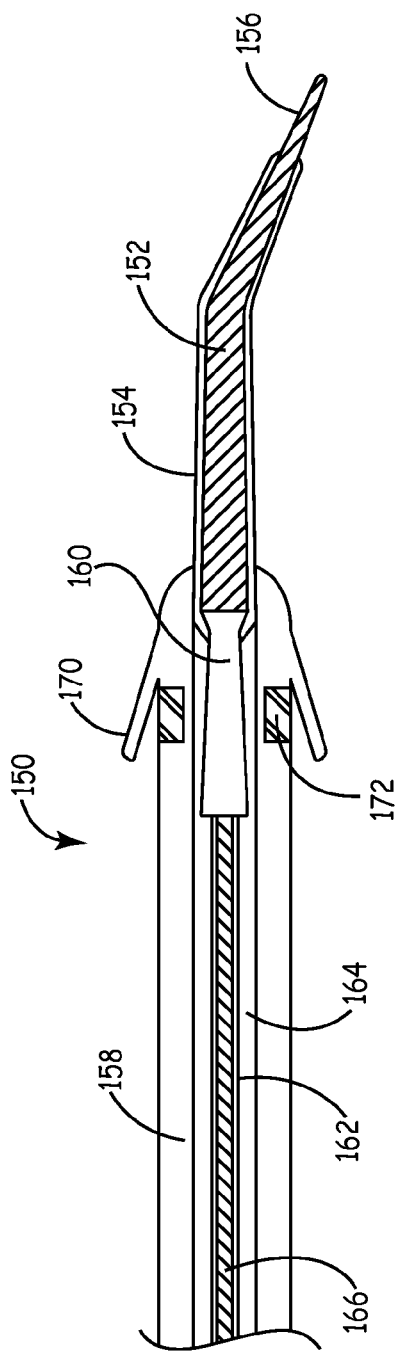
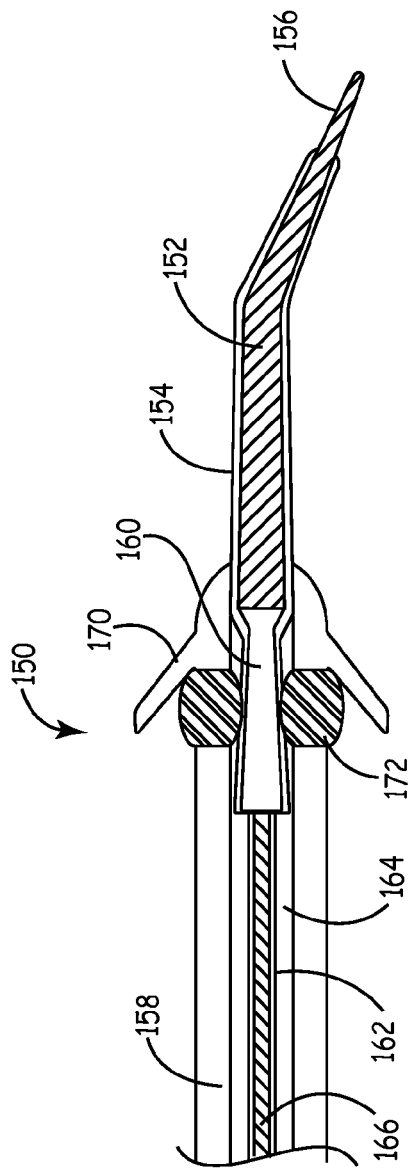

MEDICAL LEAD WITH FLEXIBLE DISTAL GUIDEWIRE EXTENSION

FIELD OF THE INVENTION

The present invention relates to an implantable medical lead and, more specifically, to a medical lead having a distal, flexible distal guidewire extension.

BACKGROUND OF THE INVENTION

Transvenous endocardial leads may be placed inside a chamber of a patient's heart by passing the lead through a venous entry site, such as the subclavian vein or the cephalic vein, or a tributary thereof, along a venous pathway into the superior vena cava and into the right cardiac chambers. Coronary or cardiac vessel leads may be advanced further, from the right atrium through the coronary sinus ostium into the coronary sinus and ultimately into one of the various cardiac vessels for stimulation and/or sensing of the left heart chambers.

Cardiac lead placement is important in achieving proper stimulation or accurate sensing at a desired cardiac location. Endocardial or cardiac vessel leads are generally implanted with the use of a guide catheter and/or a guidewire and/or stylet to achieve proper placement of the lead. A cardiac vessel lead may be placed using a multi-step procedure wherein a guide catheter is advanced into the coronary sinus ostium and a guidewire is advanced further through the coronary sinus and great cardiac vessel to a desired cardiac vessel branch. Because the tip of a guidewire is generally flexible and may be preshaped in a bend or curve, the tip of the guidewire can be steered into a desired venous branch. A cardiac lead may therefore be advanced to a desired implant location using a guidewire extending entirely through the lead and out its distal end. Cardiac leads generally need to be highly flexible in order to withstand flexing motion caused by the beating heart without fracturing. A stiff stylet or guidewire provides a flexible lead with the stiffness needed to advance it through a venous pathway. Once the lead is placed in a desired location, the guidewire and guide catheter may be removed. A guidewire placed implantable lead is disclosed in U.S. Pat. No. 6,192,280, issued to Sommer, et al. A coronary vein lead having a flexible tip and which may be adapted for receiving a stylet or guidewire is disclosed in U.S. Pat. No. 5,935,160, issued to Auricchio et al. A coronary vessel catheter or guidewire is disclosed in U.S. Pat. No. 5,509,411, issued to Littmann et al., having a plurality of sense electrode pairs for mapping electrical activity of the heart disposed proximally to a distally extending, manually shapeable, wire coil and core wire distal tip similar to a guidewire distal tip.

Cardiac vessel leads are particularly difficult to implant due to the tortuous pathway encountered as the lead is advanced through the cardiac vessels. Because of this difficulty, the surgical time required to implant a cardiac vessel lead can be considerably longer, up to 1 to 2 hours longer, than the time required to implant an endocardial lead in a right heart chamber. Placement of a cardiac vessel lead in a desired venous branch may require angling the lead end greater than 90° in order to maneuver it into the branch. Some cardiac vessel locations may therefore be inaccessible due to limitations and difficulties associated with maneuvering currently available lead systems into a narrow venous branch at an oblique, or even acute, angle.

It would be desirable, therefore, to provide a cardiac vessel lead having the physical properties needed for advancing it through a venous pathway to a desired implant site, particularly within the cardiac vessels, without the need for additional guide catheters or guidewires. The number of instruments and steps required to perform a cardiac vessel lead implantation procedure could then be reduced, making the procedure easier to perform and reducing the associated surgical time and cost.

SUMMARY OF THE INVENTION

The present invention addresses the challenges associated with implanting a medical lead in a vascular position by providing a medical lead, particularly a cardiac vessel lead, having a flexible distal guidewire extension that, in a first aspect of the invention, has a pre-formed bend along the length thereof to deflect the distal tip of distal guidewire extension away from or laterally to the longitudinal axis of the lead body, and, in a second aspect of the invention optionally combinable with the first aspect of the invention, incorporates active or passive fixation mechanisms to reduce dislodgement of the lead distal end from the site of implantation.

In one embodiment, a transvenous cardiac vessel lead is provided with a tip electrode through which a flexible distal guidewire extension extends to the distal guidewire extension distal tip. The proximal end of the distal guidewire extension is attached to a core retained within the distal end of the lead body. The core may also serve as a crimp core for electrically coupling a coiled conductor to a conductive sleeve extending proximally from the tip electrode. A stylet may be used through the lumen of the coiled conductor, which extends the length of the lead body, to aid in advancing the cardiac vessel lead.

The guidewire and core are preferably electrically isolated from the tip electrode, conductor, and conductive sleeve by insulation. A distal segment of the guidewire may be left uninsulated and serve as an electrode. Filars included in the coiled conductor may be electrically coupled to the guidewire via the core. Alternatively, a cabled or stranded conductor may be electrically coupled to the guidewire core. A cabled or stranded conductor extending through a central lumen of the lead prevents the use of a stylet. Therefore, the cabled or stranded conductor, if used, is preferably provided with a stiff insulating material that improves the pushability of the lead. In one embodiment, the guidewire may be used as a cathode electrode in place of another type of tip electrode and may extend from the distal end of the lead body.

The flexible distal guidewire extension is preferably tapered and facilitates advancement of the distal electrode(s) into a cardiac vessel, e.g., the coronary sinus, through twists and turns of the cardiac vessel and then into openings of branch vessels branching from the cardiac vessel.

In the further aspect of the present invention a cardiac vessel lead having a distal guidewire extension is provided with active or passive fixation mechanisms adapted to engage the cardiac vessel when the electrode(s) are advance to the desired site to inhibit dislodgement of the electrode(s).

In one preferred embodiment, passive fixation members such as soft, pliant tines are provided on the lead body near the lead body distal end that tend to be deflected inward to enable passage through the cardiac vessels and bear outward against the vessel wall when the electrode(s) is at a desired site. Moreover, the tines may be loaded with an anti-inflammatory steroid, and/or the lead may be provided with a monolithic controlled release device (MCRD) for eluting steroid over time. The swelling effect that occurs as steroid elutes from the tines and/or MCRD and is replaced by water may also act to provide passive fixation of the lead.

In alternative embodiments, the cardiac vessel lead may be provided with an active fixation member, such as a helical tip electrode through which the distal guidewire extension extends. The distal guidewire extension may be provided as a buffer to prevent the sharpened tip of the active fixation member from causing tissue damage as the lead is advanced. A seal may be provided to prevent the ingress of fluids at the distal end of the lead.

Advantages of the present invention include improved maneuverability of a lead without the use of a guide catheter or separate guidewires extending through the entire lead body. The lead, having a distal guidewire extension may be provided with a reduced diameter and may easily be advanced deep within the cardiac vessels. The distal guidewire extension, which may optionally be used as an electrode, allows positioning of an electrode very deep in the cardiac vessels.

BRIEF DESCRIPTION OF THE DRAWINGS

FIG. 5A is a side, cut-away view of the distal end of yet another embodiment of the present invention wherein the distal guidewire extension is also provided as a lead tip electrode.

FIG. 5B is a side, cut-away view of the distal end of the lead of FIG. 5A illustrating the effect of swelling on steroid-loaded tines and an MCRD which may be used to enhance chronic fixation of the lead in a vessel lumen.

DETAILED DESCRIPTION OF THE PREFERRED EMBODIMENTS OF THE INVENTION

Figure 1:
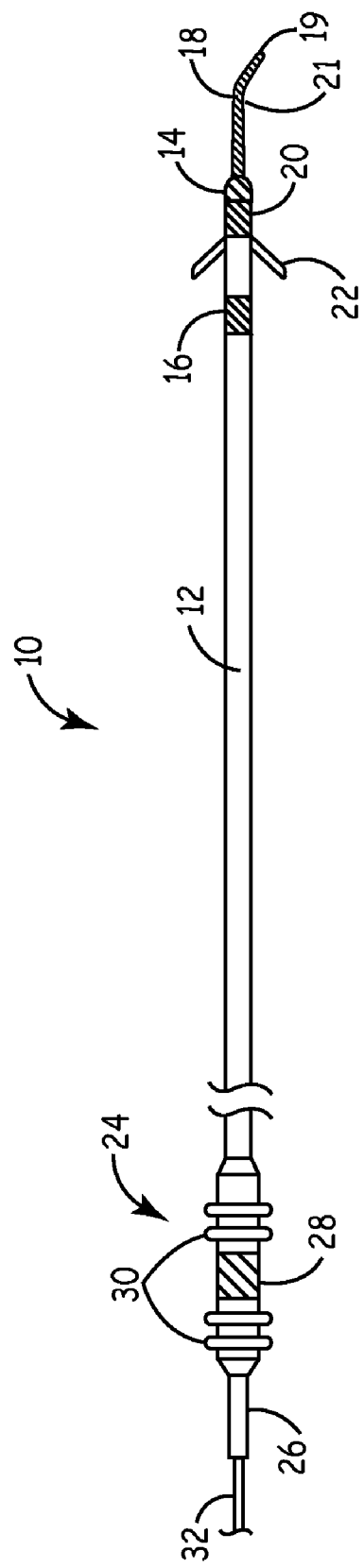
FIG. 1 is a plan view of one embodiment of a lead according to the present invention, in which the lead is provided with a flexible, distal guidewire extension.

The present invention is aimed at providing an implantable medical lead that is particularly adapted for implantation in a desired branch of a blood vessel, such as in a branch of the cardiac vessels. FIG. 1 is a plan view of one embodiment of a cardiac vessel lead 10 according to the present invention, wherein the lead 10 is provided with a flexible, distal guidewire extension 18. The lead 10 includes an elongated, lead body 12 formed from an insulating biocompatible polymer, such as polyurethane or silicone rubber. Lead body 12 is provided with at least a central lumen for carrying a conductor or may be provided as a multi-lumen lead body for carrying multiple conductors, as generally disclosed in U.S. Pat. No. 5,584,873 issued to Shoberg et al., incorporated herein by reference in its entirety. Alternatively, the lead may include additional conductors arranged concentrically in a lumen, as disclosed in U.S. Pat. No. 4,355,646 issued to Kallok et al., also incorporated herein by reference in its entirety. Lead body 12 is relatively flexible so that it is capable of withstanding the repeated flexing caused by the beating heart without fracture. Lead body 12 is preferably provided with a small outer diameter, on the order of 4 French or less, and more preferably on the order of 2 French or less, so that it may be advanced to a final location in a narrow blood vessel.

At the distal end of the lead 10 is a tip electrode 14, shown as a generally hemispherical electrode. Spaced proximally from tip electrode 14 is a ring electrode 16. Electrodes 14 and 16 are preferably formed from a conductive, biocompatible material, such as platinum, iridium, or alloys thereof. Tip electrode 14 may be, for example, a porous sintered electrode, similar to that described in U.S. Pat. No. 5,282,414 issued to Stokes et al., incorporated herein by reference in its entirety, or a ring tip electrode resembling the electrode disclosed in U.S. Pat. No. 5,342,414 issued to Mehra, also incorporated herein by reference in its entirety.

A connector assembly 24 is provided at the proximal end of lead 10 for connecting lead 10 to a further implantable medical device, e.g. an implantable pulse generator for providing cardiac pacing. Connector assembly 24 includes a pin connector 32 and a ring connector 28 which are each electrically coupled to a respective conductor extending to tip electrode 14 and ring electrode 16. Sealing rings 30 are provided for forming a fluid-tight seal with the inner surface of a connector port provided on a medical device. A stylet 32 is shown exiting the proximal end of pin connector 26. Pin connector 26 is preferably provided as a hollow pin in communication with a lumen of lead body 12 to allow introduction and advancement of a stylet 32 down the lumen of lead body 12. Stylet 32 may be used to provide lead 10 with the stiffness needed to advance lead 10 through a venous pathway.

A tapered, flexible distal guidewire extension 18 is shown exiting the distal end of tip electrode 14 and extending through a bend 21 to guidewire distal tip 19. Distal guidewire extension 18 is preferably formed as a helically wound wire coil or a wire braid of a metal such as stainless steel, nickel-titanium alloy, or platinum-iridium alloy. Distal guidewire extension 18 is provided as a highly flexible member, capable of adapting to bends and curves encountered in a tortuous venous pathway. Examples of flexible guidewire tip constructions that may be adapted for use in the present invention are generally described in U.S. Pat. No. 4,984,581 issued to Stice, and U.S. Pat. No. 5,067,489 issued to Lind, both patents incorporated herein by reference in their entirety.

In a first aspect of the present invention, distal guidewire extension 18 has a pre-formed bend at a desired angle at bend 21 for maneuvering the electrodes 14 and 16 into a desired blood vessel branch or cardiovascular structure accessed from a cardiac vessel, e.g. the coronary sinus ostium in the right atrium. The bend 21 is preferably formed at about 45° at a point about 5 mm to about 10 mm from the distal guidewire extension distal tip 19. The distal tip 19 therefore extends laterally to the axis of the lead body 12. The distal tip 19 can be rotated during advancement of the lead body 12 through the venous pathway by application of torque applied at proximal connector assembly 24 through the lead body 12 and/or the stylet 32 to aim the laterally extending distal tip 19 through a turn or into the opening of a branch cardiac vessel.

FIG. 1 also illustrates one embodiment of the second aspect of the invention wherein the lead 10 may be optionally provided with passive fixation members, e.g., flexible, pliant tines 22, which act to maintain the implanted position of lead 10 as is known in the art. Tines 22 may be loaded with an anti-inflammatory steroid for reducing the inflammatory response and thereby improve the long-term electrical properties of the electrode-tissue interface. Lead 10 may optionally be provided with a monolithic controlled release device (MCRD) 16, located just proximally to tip electrode 14, for eluting an anti-inflammatory steroid over time. An MCRD 16 may be provided as generally disclosed in U.S. Pat. No. 4,506,680 issued to Stokes or U.S. Pat. No. 4,972,848 issued to DiDomenico et al., both patents incorporated herein by reference in their entirety. The swelling of tines 22 and/or MCRD 16 as a steroid elutes out of the polymer structure and is replaced by water may further enhance fixation of the lead 10 within a vessel lumen, as will be described in greater detail below in conjunction with FIG. 5B.

Figure 2:
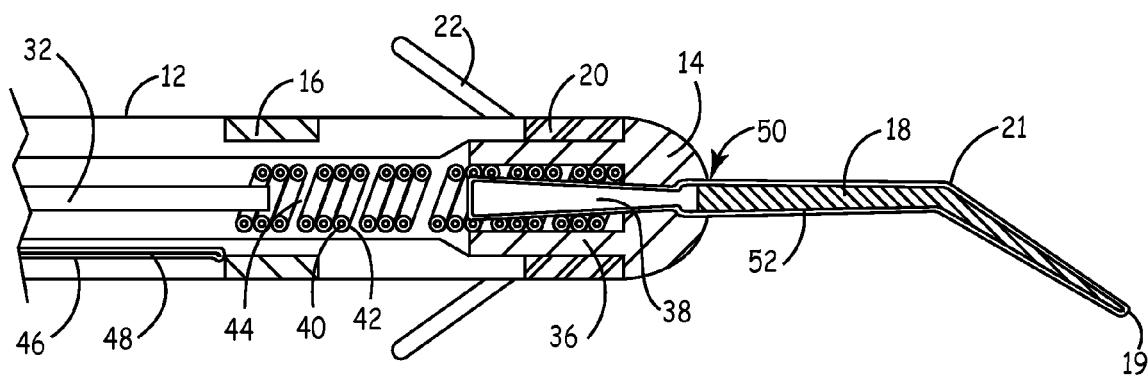
FIG. 2 is a side, cut-away view of the distal end of the lead shown in FIG. 1.

FIG. 2 is a side, cut-away view of the distal end of the lead body 12 shown in FIG. 1. Distal guidewire extension 18 is shown attached to a tapered, solid core 38. Core 38 may extend through the extension 18 and may be provided as a shape memory alloy, such as nitinol. The use of a shape memory alloy core is generally described in the above cited '581 patent. Distal guidewire extension 18 is preferably provided with insulation 52 on its exterior surface in order to prevent stimulation current that is being delivered by electrode 14 from straying to extension 18 and to the surrounding tissue in contact with extension 18. The effective electrode surface area is thereby limited to the surface area of electrode 14, maintaining a higher pacing impedance for less current drawn from an associated pacemaker battery. Insulation 52 may be provided by dip coating extension 18, and optionally core 38, in a silicone solution. Extension 18 may also be insulated by tubing formed from an appropriate plastic such as polytetrafluoroethylene (PTFE), ethylene tetrafluoroethylene (ETFE), polyurethane or otherwise.

An adhesive may be applied at the location indicated by arrow 50 in order to seal the opening of tip electrode 14, through which extension 18 passes, to prevent fluid from entering lead body 12. Tip electrode 14 is provided with an electrically conductive sleeve 36, which is electrically coupled to a conductor 40. Conductor 40 is preferably a coiled conductor and may be provided with an insulating sheath 42. If conductor 40 is a multi-filar coiled conductor, each individual filar may be surrounded by insulation 42, which may take the form of a sheath or coating of an appropriate insulating material such a PTFE, ETFE, polyurethane or polyimide. Each individually insulated filar may then be used as an electrically isolated conductor for a given electrode.

Electrical coupling of sleeve 36 to conductor 40 may be achieved by crimping sleeve 36 around conductor 40 at a location where an uninsulated portion of an appropriate filar included in conductor 40 is exposed to make electrical contact with sleeve 36. Core 38 advantageously acts as a crimp core, supporting the inner diameter of coil 40 during the crimping process and maintaining the position of coil 40 against the inner diameter of sleeve 36, thereby ensuring good electrical contact. Electrical coupling between sleeve 36 and conductor 40 may alternatively be made by welding or other appropriate methods. Coiled conductor 40 advantageously provides a central lumen 44 through which stylet 32 may be advanced until it reaches core 38.

When cardiac vessel lead 10 is provided as a bipolar lead, as shown in FIGS. 1 and 2, ring electrode 16 is electrically coupled to an appropriate conductor 48, such as a cable or stranded type conductor, extending through lumen 46 of multi-lumen lead body 12. An example of a stranded conductor that may be used in the present invention is disclosed in U.S. Pat. No. 5,246,014 issued to Williams, et al., incorporated herein by reference in its entirety. Alternatively, a filar within coil 40 may be electrically coupled to ring electrode 16, as is illustrated in FIG. 3.

Figure 3:
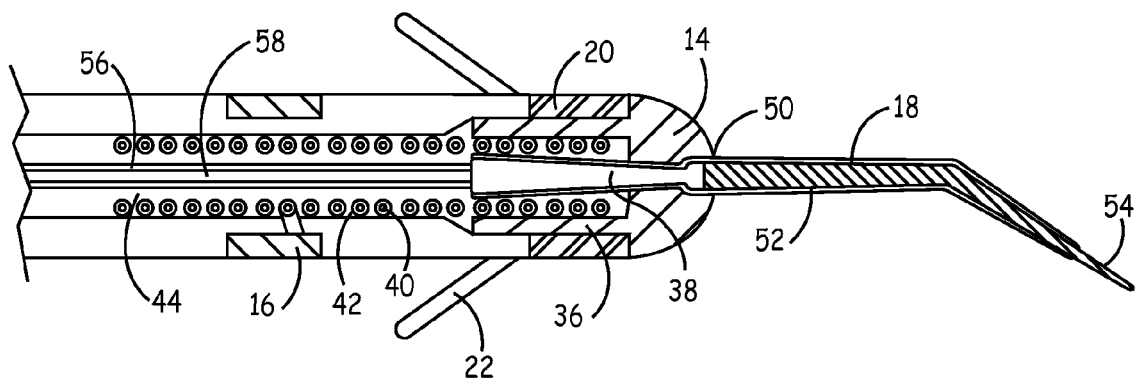
FIG. 3 is an alternative embodiment of the lead shown in FIG. 1 wherein the distal guidewire extension may also serve as an electrode.

FIG. 3 is an alternative embodiment of the lead shown in FIG. 1 wherein the flexible distal guidewire extension may also serve as an electrode. Core 38 and a portion of distal guidewire extension 18, which may be in contact with electrode 14, sleeve 36 or conductor 40, may be insulated, and a distal segment 54 of extension 18 may be left uninsulated. An appropriate filar included in multi-filar, coiled conductor 40 may be electrically coupled to core 38. An additional connector ring, corresponding to the respective filar and guidewire electrode, may be added to the proximal connector assembly 24 shown in FIG. 1 to accommodate electrical connection to the guidewire electrode.

Alternatively, as shown in FIG. 3, an insulated stranded or cabled conductor 58 may be provided extending through the center lumen 44 of coiled conductor 40 and electrically coupled to core 38. A conductor extending through lumen 44 would prevent the use of a stylet through lumen 44 for lead 10 placement. Therefore, in order to provide lead 10 with the stiffness needed for advancing lead 10 through a venous pathway, a stranded or cabled conductor 58 extending through lumen 44 is preferably provided with insulating tubing 56 having a high Young's modulus, on the order of 25,000 psi or greater, such as Pellethane 2363-55D or 75D or Genymere polyimide (Virginia Power Nuclear Services Company). A small diameter lead employing this type of insulation material that is substantially stiffer than would normally be employed in the context of a permanently implantable cardiac lead is disclosed in U.S. Pat. No. 6,366,819 issued to Stokes, incorporated herein by reference in its entirety. While initially stiff, creep that occurs in the polymer over time is expected to allow the lead to conform to a venous anatomy chronically.

Figure 4:
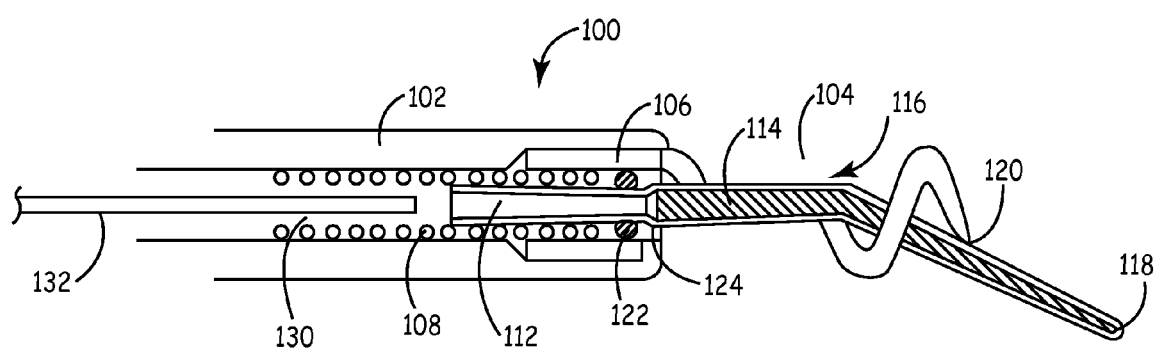
FIG. 4 is an alternative embodiment of the present invention wherein a lead is provided with an active fixation electrode and a flexible distal guidewire extension.

FIG. 4 is an alternative embodiment of the present invention wherein a lead is provided with a flexible distal guidewire extension and an active fixation mechanism that can be used to affix a distal electrode, e.g., electrode 14 of lead 10, or also optionally function as one of or the only distal electrode. For example, the lead 100 is shown as a unipolar lead having a helical electrode 104 adapted to function as a fixation helix by being rotated and screwed into cardiac tissue, e.g., a cardiac vein wall and adjacent myocardium. Active fixation mechanism and helical electrode 104 may alternatively be provided as another type of active fixation electrode, such as a barb or hook-type electrode.

In this illustrated exemplary embodiment, helical electrode 104 is electrically coupled to a conductive sleeve 106 that is further coupled to a conductor 108. Conductor 108 may be provided as a coiled conductor and may be insulated as described above in conjunction with FIG. 2. A stylet 132 may be advanced through the lumen 130 of coiled conductor 108 to aid in advancing lead 100. Alternatively, conductor 108 may be provided with a stiff insulating tube, as generally disclosed in the '819 patent cited above, to provide the lead with adequate stiffness, making the use of a stylet unnecessary. Lead 100 may optionally be provided as a bipolar or multipolar lead having additional ring and/or coil electrodes with associated conductors.

Conductive sleeve 106 may be electrically coupled to conductor 108 as described previously by crimping sleeve 106 onto conductor 108 using core 112 as a crimp core to support coil 108 on its inner diameter. The crimping procedure may act to position distal guidewire extension 114, attached to core 112, off the center axis of helical electrode 104, causing extension 114 to rest against the inner diameter of a turn in helical electrode 104 as indicated by arrow 116.

When the distal guidewire extension 114 and helical electrode 104 are axially aligned such that at least a proximal segment of the distal tip 118 of distal guidewire extension 114 is pointing in the same general direction as the tip 120 of helix 104, the distal tip 118 of distal guidewire extension 114 will act as a buffer to prevent the sharpened helix tip 120 from causing undesired tissue damage as lead 100 is advanced through a blood vessel. Distal tip 118 will glide along the inner lumen of the vessel providing a flexible atraumatic "cushion" between the blood vessel wall and the sharpened tip 120 of helix 104. Distal guidewire extension 114, being highly flexible, will bend out of the way when helix 104 is advanced into a tissue site and will therefore not interfere with fixation of helical electrode.

A generally annular seal 122 may be provided to form a fluid-tight seal with the inner surface of sleeve 106 and the outer diameter of core 112 to prevent the ingress of body fluids into the lumen of lead body 102. An annular flange 124 at the distal end of core 112 acts to retain seal 122 within the lead body 102.

FIG. 5A is a side, cut-away view of the distal end of yet another embodiment of the present invention wherein the flexible distal guidewire extension is also provided as a distal electrode. A lead 150 is shown having a lead body 158 and central lumen 164. A flexible distal guidewire extension 152 exits the distal end of lead body 158 and is attached to a core 160, which is crimped or welded to conductor 162 within lead body 158. Insulation 154 surrounds all but a distal segment 156 of distal guidewire extension 152. The distal segment 156 may then act as a cathode electrode in place of other types of tip electrodes known in the art. Core 160 is electrically coupled to a conductor 162. Conductor 162 is shown in this embodiment as a stranded or cabled conductor with insulation 166 formed from a tubing having a very high Young's modulus to improve the pushability of lead 150, as described above in conjunction with FIG. 3. Alternatively, a coiled conductor may be provided having a stiff insulating sheath or a central lumen that allows a stylet to be used to advance lead 150. Lead 150 is shown in FIG. 5A as a unipolar lead having a single electrode provided as the distal segment 156 of extension 152, however, additional ring or coil electrodes may optionally be provided in bipolar or multipolar designs, including additional conductors in a multi-filar coil or stranded cable conductor, or in a multi-lumen lead body. In bipolar or multipolar designs, the distal segment 156 of extension 152 may act as a cathode or anode electrode, paired with one or more other electrodes, for stimulation or for sensing.

Fixation of lead 150 may be achieved by providing core 160 as a shape memory alloy extending the length of extension 152. The shape memory properties may be used to bend the distal guidewire extension 152 such that it becomes lodged within a desired vessel lumen. Alternatively tines 170, a swelling MCRD 172, or other fixation mechanisms may be provided.

FIG. 5B is a side, cut-away view of the distal end of the lead 150 of FIG. 5A illustrating the effect of a swelling MCRD 172 on tines 170. This effect may be used to enhance chronic fixation of the lead 150 in a vessel lumen. In FIG. 5A, tines 170 are shown laying relatively flat along the outer diameter of lead body 158. In this position during lead implantation, tines 170 do not interfere with advancement, or retraction if necessary, of lead 150 through a narrow blood vessel. After lead implantation, steroid will elute from MCRD 172. MCRD 172 is preferably formed from silicone rubber impregnated with a sodium salt form of a glucocorticosteroid, such as the sodium salt of dexamethasone phosphate. Water will replace the steroid as it leaves the polymer structure of MCRD 172, causing it to swell, as illustrated in FIG. 5B. This swelling causes greater radial extension of tines 170, such that they will press against the inner wall of a blood vessel lumen, improving the chronic fixation of lead 150 at a cardiac vessel implant site. Blood may flow unobstructed between tines 170. When tines 170 are constructed from silicone rubber containing a sodium salt form of an anti-inflammatory steroid, such as dexamethasone sodium phosphate, tines 170 may also swell, which may further contribute to the extension of tines 170 against the vessel lumen.

Thus, an implantable medical lead having a distal guidewire extension that facilitates advancement of the lead through the twists and turns and branches of cardiac vessels, particularly cardiac vessels accessed through the coronary sinus, has been described. While the detailed descriptions provided herein refer generally to a cardiac lead having a distal guidewire extension, aspects of the present invention may be included in various types of leads or catheter or cannulae systems for use in internal body spaces. The exemplary descriptions provided herein, therefore, should not be considered limiting in regard to the following claims.

The invention claimed is:

1. An implantable cardiac vein lead comprising:
   an elongated lead body extending between a lead body proximal end and
   a lead body distal end;
   the lead body including a sidewall enclosing at least one electrical conductor;
   an elongated flexible distal guidewire extension affixed to, and extending distally from the lead body distal end to a guidewire extension distal tip, the guidewire extension including a pre-formed bend that disposes the distal tip thereof laterally beyond the lead body sidewall; and
   a distal fixation helix affixed to and extending distally from the lead body distal end, the fixation helix including a sharpened tip and being adapted to affix the lead body distal end at an implantation site, wherein at least a proximal portion of the guidewire extension distal tip and the helix sharpened tip both point in a same general direction.

2. The cardiac vein lead of claim 1, wherein the distal guidewire extension tapers from a first extension diameter in proximity to the lead body distal end down to a second extension diameter at the distal guidewire extension distal tip.

3. The cardiac vein lead of claim 1, wherein the pre-formed bend is a bend of about 45°.

4. The cardiac vein lead of claim 1, wherein the distal guidewire extension comprises a wire coil.

5. The cardiac vein lead of claim 1, wherein the distal guidewire extension comprises a wire coil covered by an electrically insulating material.

6. The cardiac vein lead of claim 1, wherein the distal guidewire extension comprises a wire braid.

7. The cardiac vein lead of claim 1, wherein the distal guidewire extension comprises a wire braid covered by an electrically insulating material.

8. The cardiac vein lead of claim 1, wherein the distal guidewire extension is electrically coupled to the at least one electrical conductor to function as an electrode.

9. The cardiac vein lead of claim 8, wherein a proximal segment of the distal guidewire extension is electrically insulated, and a distal segment of the distal guidewire extension is exposed to function as the electrode.

10. The cardiac vein lead of claim 1 wherein:
the distal fixation helix includes a helix lumen; and
the elongated flexible distal guidewire extension extends distally through the helix lumen.

11. The cardiac vein lead of claim 1, wherein the distal fixation helix is electrically coupled to the at least one conductor to function as an electrode.

12. The cardiac vein lead of claim 1, wherein:
the distal fixation helix includes an inner diameter and a center axis; and
the guidewire extension extends distally within the inner diameter of the helix being offset from the center axis.

\* \* \* \* \*